(12) United States Patent
Bergsma et al.

(10) Patent No.: US 6,376,219 B1
(45) Date of Patent: Apr. 23, 2002

(54) AMYLOSE PRODUCTS AS MATRIX FORMER FOR PROGRAMMED RELEASE SYSTEMS, PROCESS FOR PREPARING THESE AMYLOSE PRODUCTS, AND PROCESS FOR MAKING PROGRAMMED RELEASE SYSTEMS

(75) Inventors: Jacob Bergsma, Haren; Gerrit Henk Peter Te Wierik, Groningen; Jan Aten, Veendam; Anna Wilhelmina Arends-scholte, Borger, all of (NL)

(73) Assignee: Cooperatieve Verkoop-en Productievereniging Van Aardappelmeel en Derivaten Avebe B.A., Veendam (NL)

( * ) Notice: Subject to any disclaimer, the term of this patent is extended or adjusted under 35 U.S.C. 154(b) by 0 days.

(21) Appl. No.: 09/230,928

(22) PCT Filed: Aug. 5, 1997

(86) PCT No.: PCT/NL97/00454

§ 371 Date: Sep. 13, 1999

§ 102(e) Date: Sep. 13, 1999

(87) PCT Pub. No.: WO98/05688

PCT Pub. Date: Feb. 12, 1998

(30) Foreign Application Priority Data

Aug. 6, 1996 (NL) .............................. 1003747

(51) Int. Cl.$^7$ .............................. C12P 19/16; A61K 9/20
(52) U.S. Cl. .............................. 435/98; 435/99; 435/101; 424/464; 424/465; 424/468; 424/470; 424/489; 424/499; 106/210
(58) Field of Search .............................. 424/464, 465, 424/468, 470, 489, 499; 106/210; 435/98, 99, 101

(56) References Cited

U.S. PATENT DOCUMENTS 6,010,717 A * 1/2000 Arends-Scholte et al. .. 424/464

FOREIGN PATENT DOCUMENTS

WO    WO 96/09815    * 4/1996

* cited by examiner

*Primary Examiner*—Francisco Prats
(74) *Attorney, Agent, or Firm*—Hoffman & Baron, LLP

(57) ABSTRACT

The invention relates to matrix-forming amylose products for programmed release systems and a process for the preparation thereof. These amylose products have a dextrose equivalent (DE) of 5 to 10, a content of long-chain amylose of 20 to 40 wt. % on dry substance, a content of short-chain amylose of 40 to 80 wt. % on dry substance and a specific surface area of 0.4 to less than 1.0 m$^2$/g.

2 Claims, 1 Drawing Sheet

AMYLOSE PRODUCTS AS MATRIX FORMER FOR PROGRAMMED RELEASE SYSTEMS, PROCESS FOR PREPARING THESE AMYLOSE PRODUCTS, AND PROCESS FOR MAKING PROGRAMMED RELEASE SYSTEMS

The invention relates to specific amylose products suitable as matrix former for programmed release systems in the form of tablets, pellets, pills, capsules or granules. When lower down in the specification reference is made to tablets, the related designs mentioned above will also be meant.

Tablets contain, in addition to the active ingredient such as a drug (pharmacon), vitamin, cleansing agent, functional food ingredient (nutraceutical), fertilizer, growth agent, flavor, preservative, insecticide or herbicide, also specific adjuvants (excipients). These adjuvants are classified according to their functional properties, such as binders, fillers, disintegrants, matrix formers, lubricants, flavors or colors. Specific adjuvants may also have two or more functional properties.

A normal tablet gives a rapid release of the drug from the tablet. However, the properties of the tablet may be modified so as to obtain sustained release of the drug, e.g. in the gastrointestinal tract. This is referred to as programmed release, controlled release and/or sustained release. Important aims of programmed release systems are the reduction of the side effects of the drug and the enabling a lower dosing frequency. This can be realized by providing for sustained and gradual release of the drug from the release system. Thus, the drug is absorbed in the blood more gradually, and there is a better guarantee that the plasma concentration of the drug is higher than the minimum effective concentration. If it is desirable to maintain a constant blood level of the drug for a longer time, then this can often be obtained by allowing the drug to be released from the release system at a constant rate. The release with an amount constant per unit of time is designated as zero-order release or zero-order profile.

Several methods are known for the manufacture of programmed release systems. Because of their simple preparation matrix systems are often used. This preparation comprises the mixing the active ingredient, a matrix former and one or more adjuvants, followed by compression, e.g. for tabletting. Since the matrix systems slowly dissolve in the relevant water-containing environment (e.g. the gastrointestinal tract) or since slow diffusion of water takes place in the tablet, sustained release of the active ingredient is effected.

It is an object of the invention to provide amylose products which are eminently suitable as a matrix-forming component in programmed release systems such as matrix tablets. For the manufacture of these tablets the conventional techniques can be used, namely dry granulation, wet granulation and direct compression.

The amylose products provided according to the invention are in particular very suitable for the manufacture of matrix tablets via direct compression. Here the powder mixture to be tabletted is introduced into the molds of a tabletting press and then compressed into tablets with a stamp.

It is a further object of the invention to provide a simple and efficient process for preparing such amylose products.

Figure 1:
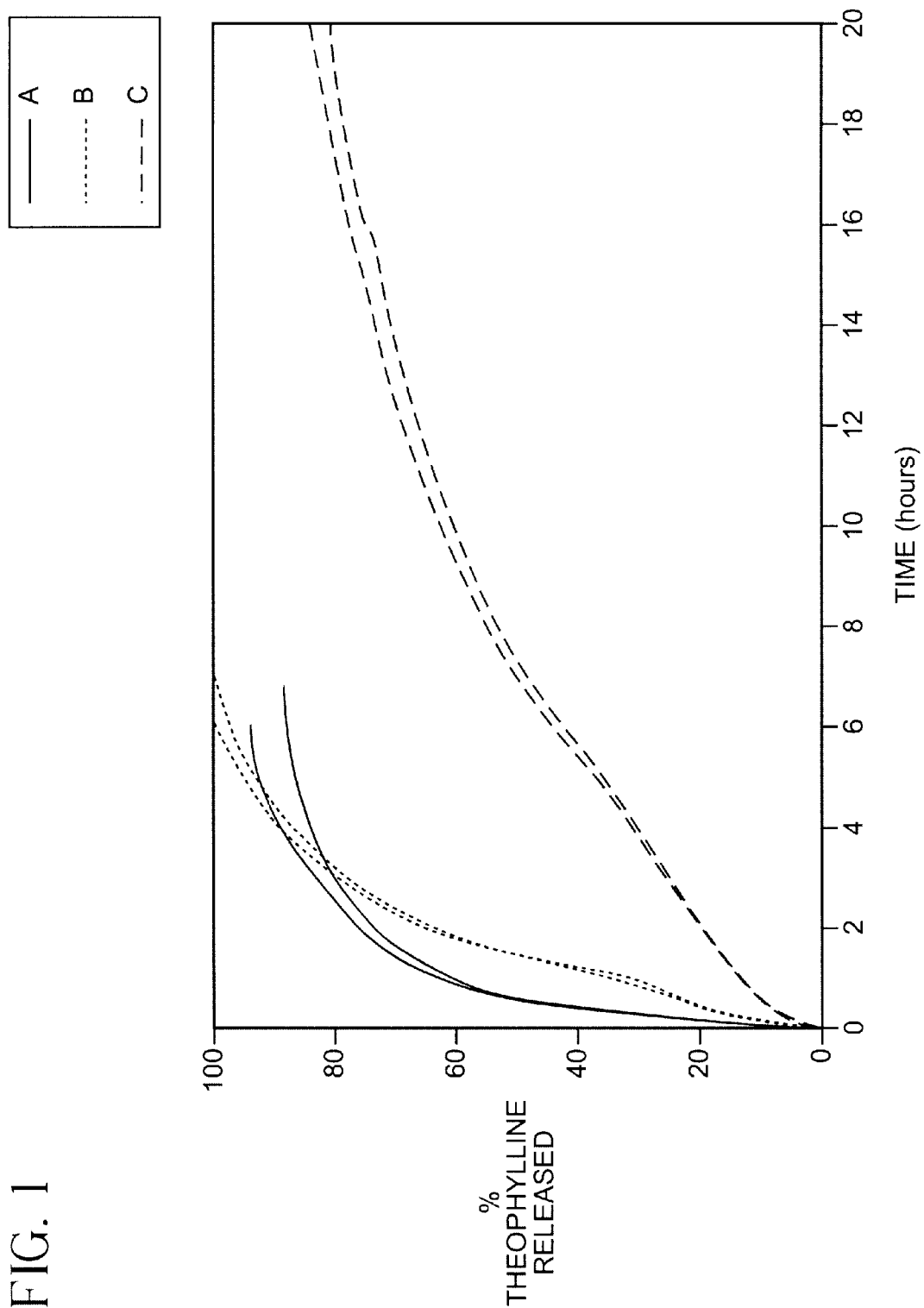
FIG. 1 depicts the release profile of theophylline from tablets prepared using the amylose component of the invention.

Most types of starch consist of granules in which two types of polymers occur, viz. amylose (15–35 wt. % on dry substance) and amylopectin (65–85 wt. % on dry substance). Amylose consists of substantially linear molecules with an average degree of polymerization (DP) of 1,000–5,000 (depending on the type of starch). Amylopectin consists of very large, highly branched molecules with an average degree of polymerization of about 2,000,000. The commercially most important types of starch, viz. maize starch, potato starch, wheat starch and tapioca starch, contain 15–30 wt. % amylose. Of some types of cereal (barley, maize, millet, milo, rice and sorghum) and of potato starch there exist varieties which nearly completely consist of amylopectin. These types of starch contain less than 5 wt. % amylose and are designated as amylopectin starches.

By debranching amylopectin molecules by means of so-called debranching enzymes, such as isoamylase and pullulanase, short-chain linear glucose polymers are obtained with a degree of polymerization substantially between 10 and 75. These products are designated here as short-chain amylose (such products are also referred to in the literature as linear dextrin or amylodextrin). This is opposed to long-chain amylose with a degree of polymerization of more than 100, which occurs naturally in starch granules or can be obtained by limited partial depolymerization of this amylose.

The use of amylose products as matrix former in programmed release systems is known. The international patent publications WO 94/01092 and WO 96/09815 describe the use of low-molecular and/or high-molecular amylose products in matrix tablets. The preparation and use of amylose products in programmed release systems is also described in the following two journal articles:

G. H. P. Te Wierek, A. C. Eissens, A. C. Besemer and C. F. Lerk: Preparation, characterization and pharmaceutical application of linear dextrins: I. Preparation and characterization of amylodextrin, metastable amylodextrins and metastable amylose. Pharmaceutical Research, Vol. 10, No. 9, 1993, pp. 1274–1279.

G. H. P. Te Wierek, J. van der Veen, A. C. Eissens and C. F. Lerk: Preparation, characterization and application of linear dextrins. Part VI, General applicability and mechanism of programmed release from amylodextrin tablets. Journal of Controlled Release, 27 (1993), October, No. 1, pp. 9–17.

In the above-mentioned publications the amylose products are broadly described. Furthermore, the preparation methods described are laborious and/or must be carried out starting from relatively expensive and scarce amylopectin starches.

A combination of characteristics of amylose products has now been found which gives an excellent matrix-forming programmed release system. A simple and efficient process for preparing such amylose products has also been found.

The amylose products used according to the invention as matrix former in the manufacture of programmed release systems are characterized by:

a dextrose equivalent (DE) of 5 to 10 and preferably of 5 to 8, a content of long-chain amylose with a degree of polymerization of more than 100 of 20 to 40 wt. % on dry substance, a content of short-chain amylose with a degree of polymerization between 10 and 75 of 40 to 80 wt. % on dry substance, a specific surface area between 0.4 and less than 1.0 m$^2$/g and preferably at least 0.7 m$^2$/g.

For completeness sake, it is pointed out that maximally 40 wt. % amylose with a DP<10 and/or a DP between 75 and 100 may be present.

The amylose products according to the invention are prepared from types of starch containing at least 15 wt. % (on dry substance) of amylose. Suitable types of starch are potato starch, maize starch, tapioca starch, wheat starch, sago starch, rice starch, and pea starch. The starting material used for the preparation of the amylose products according to the invention may also be modified starches obtained by chemical, enzymatic and/or physical modification of the above-mentioned native amylose-containing types of starch.

In the preparation of the amylose products according to the invention an aqueous starch solution is treated with an α-amylase (EC 3.2.1.1.) and a debranching enzyme such as an isoamylase (EC 3.2.1.68) or a pullulanase (EC 3.2.1.41). These treatments take place simultaneously or in the order of first α-amylase and then the debranching enzyme. By the action of α-amylase the starch molecules are partially depolymerized. By the action of the debranching enzyme the amylopectin molecules are converted into short-chain amylose.

The enzymatic reactions are carried out in aqueous medium. The starch solution to be used can be prepared by heating an aqueous starch suspension above the gelatinization temperature of the starch, e.g. by means of a steam jet device (usually designated as jet cooker). The starch concentration of the starch solution is preferably between 3 and 40 wt. %. The enzymatic reactions are preferably carried out at a pH between 4 and 8 and a temperature between 40 and 70° C. The reaction time is preferably between 4 and 100 hours.

If α-amylase and debranching enzyme are allowed to act on the starch solution simultaneously, very suitable matrix-forming amylose products are obtained. If first α-amylase and then a debranching enzyme is allowed to act, suitable amylose products can also be obtained. However, if first the debranching enzyme and then the α-amylase is allowed to act, no useful amylose products are eventually obtained. If only a debranching enzyme is used, without using α-amylase, no suitable matrix formers are obtained either.

After the enzymatic reactions have proceeded to the desired extent, this is after the desired DE and the desired contents of long-chain and short-chain amylose have been obtained—the DE value determined here is higher than that of the finally recovered washed and dried final product—, the enzymatic reactions can be stopped, e.g. by lowering the pH of the reaction medium to 2–3. The reaction mixture is then slowly stirred, e.g. for 10 to 24 hours at 10 to 25° C., while isolable flocks are formed by ripening. These amylose flocks are isolated from the reaction medium by filtration, centrifugation or separation. The isolated amylose product is then washed with water, e.g. by repeatedly suspending in water and subsequent isolation. The isolated amylose product is then dried by one of the conventional drying techniques. However, this requires such drying conditions that the resulting dried amylose product has a specific surface area between 0.4 and <1.0 m$^2$/g and preferably at least 0.7 m$^2$/g. A very suitable drying technique is vacuum drying, which may be carried out, e.g. at 20 to 60° C. The final moisture content of the dried amylose product is preferably between 5 and 20 wt. %. By the action of the enzymes the final product consists as to 40 to 80 wt. % short-chain amylose. The dextrose equivalent (DE) of the washed amylose product is between 5 and 10 and preferably between 5 and 8.

To prevent friction between the tabletting powder and the tabletting machine during the preparation of tablets, magnesium stearate is often added as a lubricant. When using the amylose products according to the invention, a zero-order profile can be obtained with and without using magnesium stearate. Besides, the tabletting powder may contain yet other adjuvants such as flavors, colors, disintegrants, preservatives, pH controllers and dissolving adjuvants.

Preferably, the tablets according to the invention are manufactured by direct compression. Here the pharmacon is mixed with the amylose products as matrix former and, if necessary, with other adjuvants. The powder mixture may then be directly compressed into tablets or other release forms. Direct compression has the great advantage that the tabletting mixture need not first be subjected to (wet or dry) granulation, before it can be compressed.

The invention will be further explained by means of the following example. In the text, examples and claims reference is made to a number of concepts and determination methods which will be specified hereinafter (SW 56).

Dextrose Equivalent (DE)

Dextrose equivalent (DE) is the reducing power of a starch hydrolysate expressed as D-glucose and calculated on the dry substance. The DE was determined here by the Luff-Schoorl method.

Moisture Content

The moisture content of the powders was determined by drying 5 g product to a constant weight on a moisture balance at 105° C. The moisture content is determined from the loss of weight.

Specific Surface Face (BET)

The specific surface area (BET) was determined by means of nitrogen adsorption with a Quantasorp gas adsorption appliance (Quantochrome Corp., Syosset U.S.A.).

Programmed Release Experiments

Programmed release experiments (controlled release) with tablets were carried out in a paddle appliance (Prolab, Rhône-Poulenc, Paris, France) under conditions as specified in the USP XXI. The medium (1000 ml 50 mM phosphate buffer, pH 6.8) was deaerated. The experiments are carried out at 37° C. The rate of stirring is 100 rpm. The concentrations of the pharmacon were determined spectrophotometrically by means of an Ultrospec 40S2 TDS appliance (LKB, Zoetermeer) at 268 nm. The experiments were carried out in duplicate.

Amylose Content

The contents of long-chain and short-chain amylose in the washed amylose products were determined by means of gel permeation chromatography (GPC).

EXAMPLE

In this example the preparation, properties and use (as matrix former) of amylose products according to the invention (C) are compared with amylose products which do not satisfy the specifications of the invention (A and B).

(A)—Only Debranching

A suspension of 366 g potato starch (with 19 wt. % moisture) in 1634 g mains water was gelatinized in a jet cooker at 160° C. The resulting starch solution (with 14 wt. % dry substance) was adjusted to pH 4.5 and cooled to 57° C. Then 2% (w/w on dry substance) Optimax 300 L (a debranching enzyme preparation of Solvay Enzymes) was added. After a reaction time of 48 hours the DE of the reaction mixture was 5.3. Then pH was adjusted to 7, and the reaction mixture was cooled to 15° C. After ripening for 17 hours the flock-shaped amylose product was separated by means of filtration on cloth. The soluble fraction was washed by repeatedly suspending in water and filtration. This was repeated until the washing liquor contained less than 1 wt.

% dry substance. The filter cake (19.5 wt. % dry substance) was vacuum dried at 20° C. The moisture content of the final product was 16.3% (w/w) and the DE 4.5.

(B)—Debranching, Followed by Treatment with α-amylase

A suspension of 366 g potato starch (with 19 wt. % moisture) in 1634 g mains water was gelatinized in a jet cooker at 160° C. The resulting starch solution (14 wt. % dry substance) was adjusted to pH 4.5 and cooled to 57° C. Then 2% (w/w on dry substance) Optimax 300 L (a debranching enzyme preparation of Solvay Enzymes) was added. After a reaction time of 48 hours the DE of the reaction mixture was 5.3. After adjusting the pH to 6.5 and increasing the temperature to 71° C., 0.014% (w/w on dry substance) of the thermostable α-amylase G-zyme G 995 (preparation of Rhône-Poulenc) was added. After a reaction time of 20 minutes the DE of the reaction mixture was 8.0. The reaction was stopped by lowering the pH to 2.5. After ripening for 17 hours at 15° C. and adjusting the pH to 7.0 the resulting flock-shaped amylose material was regenerated as described under (A). The moisture content of the final product was 7.2% (w/w) and the DE 5.7.

(C)—Debranching in the Presence of α-amylase

A suspension of 366 g potato starch (with 19 wt. % moisture) in 1634 g mains water was gelatinized in a jet cooker at 160° C. The resulting starch solution (14 wt. % dry substance) was adjusted to pH 4.5 and cooled to 57° C. Then 2% (w/w on dry substance) Optimax 300 L (a debranching enzyme preparation of Solvay Enzymes) and 0.0013% (w/w on dry substance) α-amylase Fungamyl 800 L (preparation of NOVO Nordisk A/S obtained from *Aspergillus oryzae*) was added. After a reaction time of 24 hours the DE of the reaction mixture was 8.0. The reaction was stopped by lowering the pH to 2.4. After ripening for 17 hours at 15° C. and adjusting the pH to 7.0 the resulting flock-shaped amylose material was regenerated as described under (A). The moisture content of the final product was 15.2% (w/w) and the DE 6.5.

In Table 1 the preparation and properties of the 3 amylose products A, B and C are mentioned.

TABLE 1

Preparation, properties and use of amylose products A, B and C

| Amylose product | Preparation | DE washed product | Wt. % long-chain amylose on d.s. (DP > 100) | Wt. % short-chain amylose on d.s. (10 < DP < 75) | Specific surface area in m²/g | Release profile |
|---|---|---|---|---|---|---|
| A | Only debranching | 4.5 | 52 | 48 | 0.2 | Very rapid |
| B | Debranching and then α-amylase | 5.7 | 45 | 55 | 0.9 | Rapid |
| C | Debranching and simultaneously α-amylase | 6.3 | 35 | 65 | 0.9 | Slow (zero order) |

The resulting 3 amylose products were tested as matrix former in tablets with programmed release (controlled release). To this end, the amylose product (70 wt. %) was mixed with the pharmacon theophylline (30 wt. %) in a Turbula mixer for 30 minutes. This physical mixture was then mixed with 0.5 wt. % magnesium stearate in a Turbula mixer for 2 minutes. Of these mixtures tablets were formed at 15 kN. The release profile of the tablets is shown in FIG. 1 and listed in Table 1. When using the amylose products according to the invention (C) the pharmacon is released with the desired zero-order kinetics. Tablets manufactured with amylose product A or B (not according to the invention) rapidly to very rapidly disintegrate and are therefore not suitable as matrix former in programmed release systems. Tablets manufactured with amylose product C (according to the invention) substantially do not disintegrate during release of the drug in the gastro-intestinal tract.

What is claimed is:

1. A process for preparing an amylose product, which comprises long-chain amylose with a degree of polymerization of more than 100 of 20 to 40 wt. % on dry substance, and short-chain amylose with a degree of polymerization between 10 and 75 of 40 to 80 wt. % on dry substance, wherein the product has a dextrose equivalent of 5 to 10, wherein the product has a specific surface area, as determined by means of nitrogen adsorption, between 0.4 and less than 1.0 m²/g, and wherein the product forms a mattix thereby allowing programmed release of an active ingredient when the product is mixed with the active ingredient; comprising:

treating an aqueous solution of starch with an α-amylase and a debranching enzyme, wherein the α-amylase and the debranching enzyme act on the starch simultaneously, isolating the amylose product from the aqueous solution, wherein the amylose product is in the form of flocks in the aqueous solution, and then drying the amylose product by vacuum drying.

2. A process for preparing an amylose product which comprises long-chain amylose with a degree of polymerization of more than 100 of 20 to 40 wt. % on dry substance, and short-chain amylose with a degree of polymerization between 10 and 75 of 40 to 80 wt. % on dry substance, wherein the product has a dextrose equivalent of 5 to 10, wherein the product has a specific surface area, as determined by means of nitrogen adsorption, between 0.4 and less than 1.0 m²/g, and wherein the product forms a matrix thereby allowing programmed release of an active ingredient when the product is mixed with the active ingredient; comprising:

i) treating an aqueous solution of starch with an α-amylase and allowing the α-amylase to act;

ii) treating the aqueous solution of starch, which was treated with the α-amylase, with a debraniching enzyme, wherein steps i) and ii) are carried out consecutively;

iii) isolating the amylose product from the aqueous solution wherein the amylose product is in the form of flocks in the aqueous solution; and iv) drying the amylose product by vacuum drying.

* * * * *